(12) United States Patent
Bruder (10) Patent No.: US 6,435,714 B1
(45) Date of Patent: Aug. 20, 2002

(54) X-RAY DIAGNOSTIC DEVICE

(75) Inventor: Herbert Bruder, Hoechstadt (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 09/624,230

(22) Filed: Jul. 24, 2000

(30) Foreign Application Priority Data

Aug. 4, 1999 (DE) .......................................... 199 36 679

(51) Int. Cl.$^7$ ................................................ H05G 1/02
(52) U.S. Cl. ...................................... 378/196; 378/197
(58) Field of Search ................................. 378/146, 189, 378/193, 195, 196, 197

(56) References Cited

U.S. PATENT DOCUMENTS

| | | | | |
|---|---|---|---|---|
| 5,592,523 A | * | 1/1997 | Tuy et al. ....................... | 378/19 |
| 5,717,735 A | * | 2/1998 | Ramsdell et al. ........... | 378/208 |
| 5,835,555 A | * | 11/1998 | Barry et al. ................. | 378/146 |
| 5,838,765 A | * | 11/1998 | Gershman et al. .......... | 378/196 |
| 6,217,214 B1 | * | 4/2001 | Cabral et al. ................ | 378/196 |

FOREIGN PATENT DOCUMENTS

DE PS 198 39 825 10/1999

* cited by examiner

Primary Examiner—Robert H. Kim
Assistant Examiner—Jurie Yun
(74) Attorney, Agent, or Firm—Schiff Hardin & Waite (57) ABSTRACT

An x-ray diagnostic device has an x-ray source, with a two dimensional detector arranged opposite thereto for detecting x-rays emitted from the x-ray source as a conical x-ray beam, and with a positioning device for an examination subject arranged between the x-ray source and the detector. The x-ray source in tandem with the detector can be rotated in an oscillating manner around a system axis. The x-ray source and the detector, and the positioning device are linearly adjustable relative to one another substantially in the direction of the system axis and a computer reconstructs images of the examination subject from the output signals of the detector occurring thereby.

7 Claims, 5 Drawing Sheets

X-RAY DIAGNOSTIC DEVICE

BACKGROUND OF THE INVENTION

1. Field of the Invention

The present invention is directed to an x-ray diagnostic device of the type having an x-ray source with a two-dimensional, i.e. planar, detector arranged opposite thereto for x-rays emitted by the x-ray source as a conical, e.g. spherical or pyramid-shaped, x-ray beam, and with a positioning device for an examination subject arranged between the x-ray source and the detector, wherein the x-ray source can be rotated in tandem with the detector around a system axis and a computer reconstructs images of the examination subject from the output signals of the detector thereby obtained.

2. Description of the Prior Art

X-ray diagnostic devices are known, wherein the x-ray source and the detector are mounted opposite each other at an arc-shaped support. Since the x-ray source and the detector thus are not mounted at a closed ring, differing from conventional computed tomography, such x-ray diagnostic devices are particularly suited for intra-operative application because a patient located on the positioning device is easily accessible due to the arc-shaped support.

The output data of the detector that are acquired due to the arc-shaped structure of the support given only a partial (incomplete) circuit of the x-ray source and detector around the system axis, are reconstructed to produce images of slices of the examination subject using a 3D-back projection algorithm that is related to the Feldkamp-algorithm, as is for the conventional computed tomography (see L. A. Feldkamp, L. C. Davis, J. W. Kress, "Practical Cone Beam Algorithm", J. Opt, Soc. Am., Vol. A6, pp. 612–619, 1984). This reconstruction method is suitable for a small angle of beam spread of the x-ray beam and thereby of the detector system. Image artefact must be expected, however, for slices of the examination subject to be reconstructed, that lie far outside of the center plane, i.e. that plane which is at a right angle to the system axis that contains the focus of the x-ray source. While these artefacts are not detectable in the case of high contrast applications (employing x-ray devices of the initially described type as described in H. Barfuβ, Digital 3D-Angiography, VDE-Technical Report Volume 54: The Digital Hospital, VDE-Publishing, 1998), they cannot be ignored for low contrast applications. This permits images only of a limited area of the examination subject to be reconstructed free of image artefacts at least for low contrast applications with x-ray diagnostic devices of the initially described type.

In computed tomography, this problem can be addressed by spiral scanning of the examination subject, wherein the x-ray source and the detector, and the positioning device with the examination subject lying thereon, are shifted linearly relative to one another with continuous rotation of the x-ray source and detector around the system axis. Such a procedure is ruled out, however, in the case of x-ray diagnostic devices of the initially described type having an arc-shaped support for the x-ray source and the detector, because a continuous rotation of x-ray source and detector around the system axis is precluded in the case of such a structure.

SUMMARY OF THE INVENTION

An object of the present invention is to provide an x-ray diagnostic device of the type initially described wherein larger volume areas of an examination subject can be scanned without continuous rotation of x-ray source and detector around the system axis.

This object is inventively achieved in an x-ray diagnostic device having an x-ray source with a two dimensional detector arranged opposite thereto for x-rays emitted by the x-ray source as a conical x-ray beam, and with a positioning device for an examination subject disposed between the x-ray source and the detector, wherein the x-ray source can be rotated in an oscillating fashion in tandem with the detector around a system axis, and at the same time, the x-ray source and the detector and the positioning device are linearly mounted relative to one another substantially in the direction of the system axis, and when a computer reconstructs images of the examination subject from the output signals of the detector obtained by such scanning.

In contrast to conventional computed tomography, an oscillating rotation of the x-ray source and the detector around the system axis takes place in the case of the inventive x-ray diagnostic device, while, at the same time, the x-ray source and the detector and the positioning device on the other are moved relative to one another in the direction of the system axis. In this manner, it is possible to also scan larger volumes of an examination subject without continuous rotation of the x-ray source and detector around the system axis. Due to the two dimensional detector and the spherical or pyramid-shaped configuration of the x-ray beam, the examination subject is completely scanned in the direction of the system axis given adequate amplitude of the oscillating rotation and given a speed of the relative movement between x-ray source and detector and the positioning device which is not too fast, the limitation associated with x-ray diagnostic devices of the initially described type of being to produce images free of image faults only in a limited volume is eliminated.

In a preferred embodiment of the invention, the x-ray source and the detector are mounted opposite one another at an arc-shaped support. In the case of the support being a C-arm, its center axis substantially coincides with the system axis and the C-arm is moved back and forth around its center axis to generate the joint oscillating rotation of the x-ray source and detector. As experience from x-ray angiography shows, a C-arm offers medical personnel good access to a patient to be examined and, if necessary, treated.

In order to enable a complete scanning of the examination subject, the oscillating rotation ensues in one version of the invention with an amplitude that is at least equal to 180° plus the angle of the beam spread, with the angle of the beam spread emitted from a focus of the x-ray source being measured in the center plane.

In order to assure a complete scanning of the examination object in the direction of the system axis, in a further version of the invention the x-ray source and the detector, and the positioning device, are shifted relative to one another in the direction of the system axis by an amount (distance) per period of the oscillating movement, that is at most equal to $\Delta Z_{max}$, with $$\Delta z_{max} = \Delta_{det} \cdot \frac{R_f - \Delta_{Obj}/2}{R_f + R_d}$$

wherein $\Delta_{det}$: width of the detector measured in the direction of the system axis $\Delta_{obj}$: span of the area to be scanned of the examination subject measured transverse to the direction of the system axis $R_f$: distance of the focus of the x-ray source from the system axis, and $R_d$: distance of the detector from the system axis.

In a further embodiment of the invention, the computer calculates individual image points on the basis of those x-rays passing through the respective image points at different projection angles in the reconstruction of images of the examination subject, which have the smallest gradient relative to the center plane.

In a preferred embodiment of the invention, the computer calculates individual image points for the reconstruction of images of the examination subject on the basis of x-rays passing through the respective image point at different projection angles, with several x-rays exhibiting different gradients relative to the center plane being taken into consideration in a weighted average per projection angle, with the result that the x-ray dose applied to the examination subject being better utilized.

DESCRIPTION OF THE PREFERRED EMBODIMENTS

Figure 1:
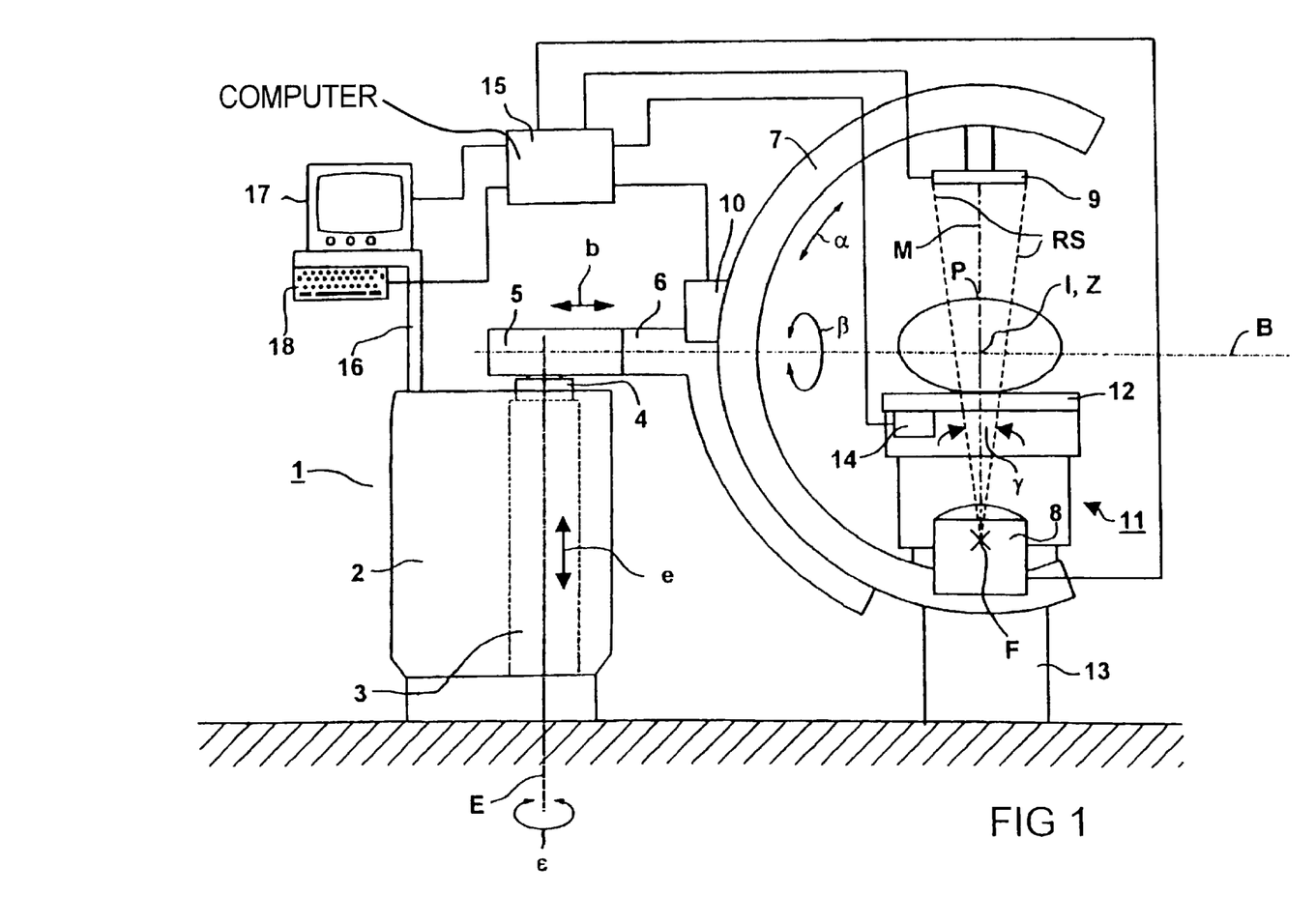
FIG. 1 is a front view of an inventive x-ray diagnostic device.
Figure 2:
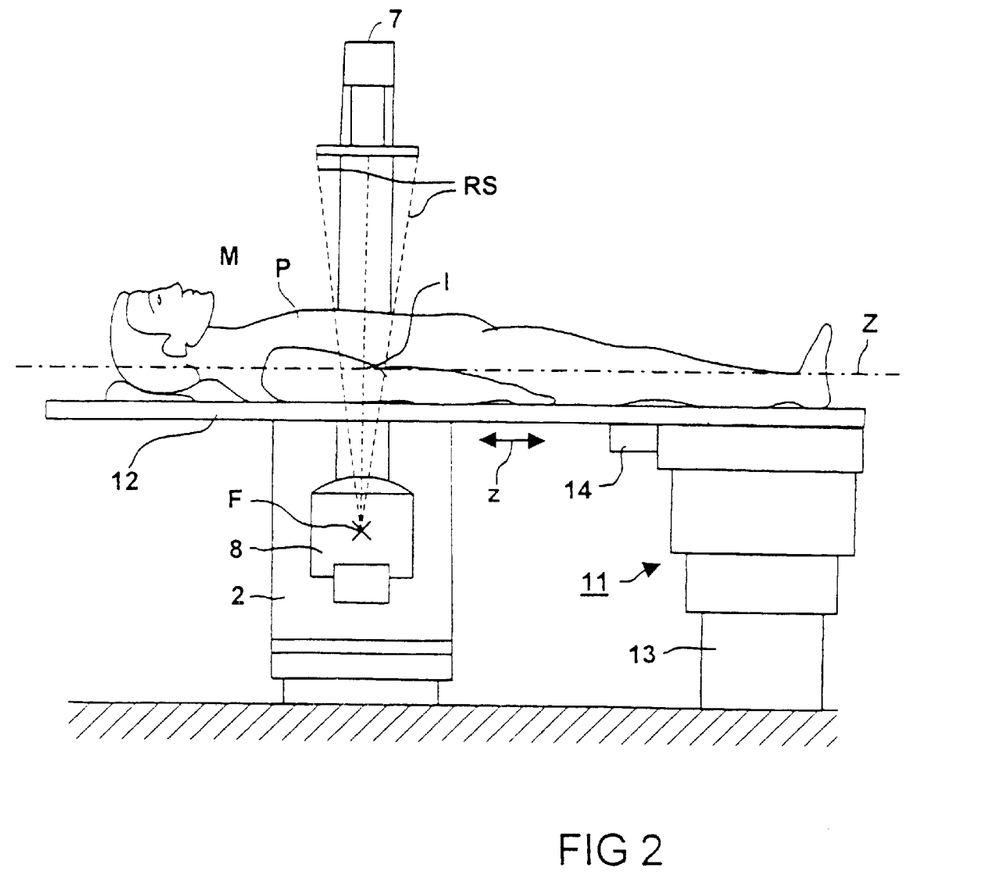
FIG. 2 is a side view of the x-ray diagnostic device according to FIG. 1.

FIGS. 1 and 2 show an inventive x-ray diagnostic device 1 that has a base or pedestal 2 at which a column 4 with a longitudinal axis E is mounted so as to be adjustable in height in the direction of the double arrow "e" using a lifting device 3 schematically indicated in FIG. 1. The column 4 is rotatable around its longitudinal axis E in the direction of the double arrow ε.

A holder 5 is mounted at the column 4, at which a support 6 is attached in turn for a C-shaped and thus open support (C-arm 7) that is adjustable around an isocenter I (in a manner described below).

An x-ray source 8 emits an x-ray beam from its focus F. the x-ray beam being indicated by edge rays RS shown with dashed lines. The x-ray source 8 and a detector 9 are mounted across from one another at the C-arm 7, so that the central ray M (passing through the isocenter I) the x-ray beam is incident approximately in the middle of the detector 9. The detector 9 is a planar detector, e.g. an x-ray image intensifier or a flat image detector as in the case of the exemplary embodiment shown in the figures. A flat image detector exhibits a number of matrix-type detector elements that are arranged in e.g. perpendicular detector columns and lines in a detector plane. The detector 9 is arranged at the C-arm 7 relative to the radiation emitter 8 so that the central point M is at a right angle to the detector plane and the detector columns run parallel to a system axis Z passing through the isocenter 1.

The C-arm 7 is mounted at the support 6 so as to be adjustable around the isocenter I and thus around the system axis Z in a known fashion in the direction of the double arrow α along its circumference, using a schematically illustrated drive 10. The system axis Z is vertical to the plane of the drawing of FIG. 1 and thus is vertical to that plane in which the focus of the x-ray source 8 moves in that α direction for the adjustment of the C-arm 7. This latter plane is identified in the following as the center plane. The drive 10 contains, e.g. an electric motor and a mechanism coupling the motor with the C-arm 7.

Figure 3:
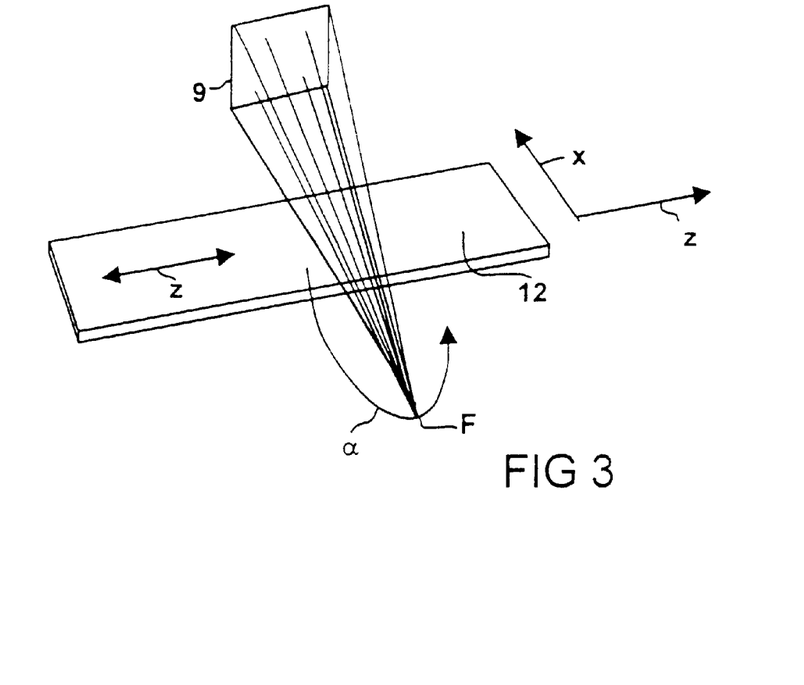
FIG. 3 shows the basic components and movement directions of the x-ray diagnostic device in schematic and perspective representation according to FIG. 1 and 2.

The C-arm 7 is rotatable with the support 6 in a known fashion in the direction of the curved double arrow β around a common axis B (of the holder 5 and the support 6) passing through the isocenter I and passing at a right angle to the system axis Z, and is seated at the holder 5 so as to be movable in the direction of the axis B (in accordance with double arrow "b") transverse to the system axis Z and thus parallel to the x-axis of the right angle coordinate system shown in FIG. 3.

For an examination subject to be examined using the inventive x-ray diagnostic device, e.g. a patient P, a positioning device 11 is provided that has a positioning plate 12 for the patient P. The plate 12 is attached at a base 13 so as to be adjustable in the direction of its longitudinal axis using a drive 14, which is depicted by a double arrow z.

The inventive x-ray diagnostic device 1 makes it possible to scan a volume of the patient P by recording two dimensional projections (datasets) from different projection angles α, and a computer 15 reconstructs three dimensional image information (regarding the scanned volume of the patient P) from the measurement data corresponding to the recorded projections, i.e. the output signals of the detector 9 that represent one measurement value per detector element for each projection. The information can be displayed, for example, in the form of slice images on a monitor 17 mounted on a holder 16 attached at the device carriage 2 and connected to the computer 15. Also connected to the computer 15 is a keyboard 18 that is also mounted at the holder 16 and serves for the operation of the x-ray diagnostic device 1, for which purpose the computer 15 is also connected to the x-ray source 8 in order to control x-ray source 8.

For recording projections from different projection angles α, the C-arm 7 with the x-ray source 8 and the detector 9 is rotated along its circumference in the direction of the double arrow α over an angle range that amounts to exactly 180° plus the fan angle γ. This rotation ensues in the case of the inventive x-ray diagnostic device 1 by periodically oscillating, while the positioning plate 12 is shifted in the direction of the system axis Z, i.e. in the one or other direction of the double arrow z, and thus parallel to the z-axis of the rectangular coordinate system shown in FIG. 3. The computer 15 controls the drives 11 and 15 so that a (preferable constant) path speed of the focus F of the x-ray source 8 results relative to the positioning plate 12.

Figure 4:
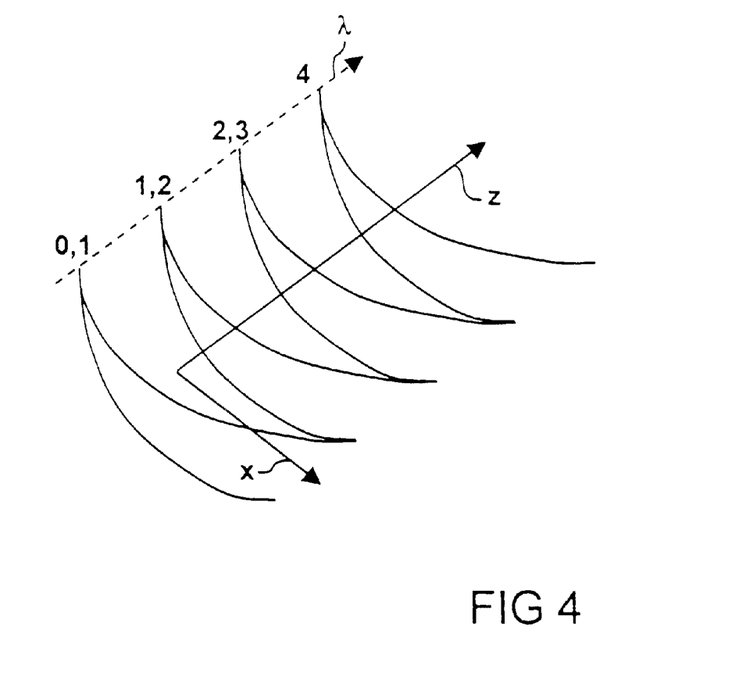
FIG. 4 shows the movement path of the focus of the x-ray source of the x-ray diagnostic device according to FIG. 1 relative to the positioning device.

The periodic, oscillating rotation of the C-arm 7 (as depicted in FIG. 4) in the α direction in an angle range $0° \leq \alpha \leq \alpha_{max}$ around the system axis Z ($\alpha_{max} < 360°$ at the C-arm 7 due to the attachment of the x-ray source 8 and detector 9) and the linear relative movement (also depicted in FIG. 3) between the radiation source 8 and detector 9, and the positioning plate 12 and patient P, in the direction of the system axis Z (in the z-direction) produces a scanning compiled in a zigzag fashion from spiral sections. The path of the focus F of the x-ray source 8 for the scan is depicted in FIG. 4, wherein λ identifies the respective periods of the rotations and the periods λ=0 . . . 4 are depicted in FIG. 4.

Figure 5:
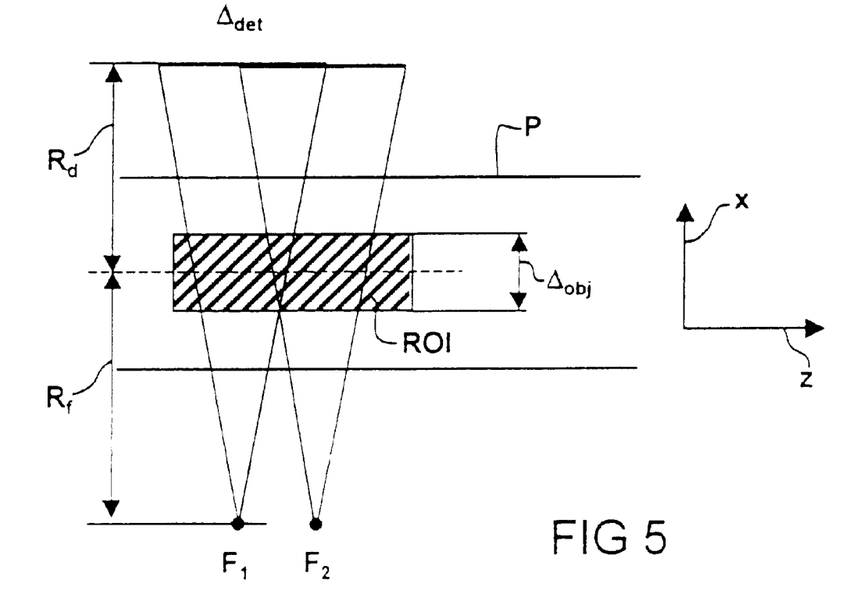
FIG. 5 illustrates the geometric relationships to be taken into consideration in conventional complete scanning of the examination subject in the direction of the system axis and around the circumference.

Since the patient P will be radiographed by a conical x-ray beam on the basis of the planar detector 9 from every position of the focus F of the x-ray source 8 in the manner evident from FIG. 1 and 2 in connection with FIG. 3, the patient P, or region of interest ROI, will be completely scanned in the z-direction in a manner evident from FIG. 5, in so far as the advance in the z-direction does not exceed a maximum allowable value $\Delta z_{max}$ per period of rotation. The following is applicable:

$$\Delta z_{\max} = \Delta_{det} \cdot \frac{R_f - \Delta_{Obj}/2}{R_f + R_d}$$

wherein according to FIG. 5:

$\Delta_{det}$: measured width of the detector in the direction of the system axis, Δobj: measured span of the ROI of the patient to be scanned transverse to the direction of the system axis Z, $R_f$: distance of the focus of the x-ray source from the system axis Z, and $F_d$: distance of the detector from the system axis Z.

The amplitude of the oscillating rotation of the C-arm 7 and thus the maximum projection angle $\alpha_{max}$ should amount to at least $80°\gamma_{fan}$, wherein $\gamma_{fan}$ is the fan angle, i.e. the angle of beam spread is in the center plane. After scanning across such a projection angle area, the patient P is scanned completely in the α-direction. Indeed, the scan thickness varies so that a conformation must be effected by applying a suitable weighting function. This reconstruction technique is referred to as "shortscan" reconstruction (see D. L Parker, "Optimal Short Scan Convolution Reconstruction for Fan Beam CT", Med. Phys. 9, pp. 254–257, 1982). This type of reconstruction and weighting is imperative in the case of the inventive x-ray diagnostic device because the projection angle region therefor necessarily always amounts to less than 360° as a result of the attachment of the x-ray source 8 and detector 9 at an open C-arm 7.

In the event that the patient P is detected completely by the x-ray beam in the center plane, the computer 15 reconstructs image data from those measurement data that are recorded in the projection angle range $0° \leq \alpha \leq \alpha_{max}$ with the application of a conical x-ray beam.

This method is similar to the Feldkamp-algorithm (see L. A. Feldkamp, L. C. Davis J. W. Kress, "Practical Cone Beam Algorithm", J. Opt. Soc. Am., Vol A6, pp. 612–619, 1984) for the processing of conical measurement data that are measured on a complete circuit. The two dimensional back projection method described therein for the two dimensional inversion of the radon formula is expanded in a natural fashion to a three dimensional back projection.

Figure 6:
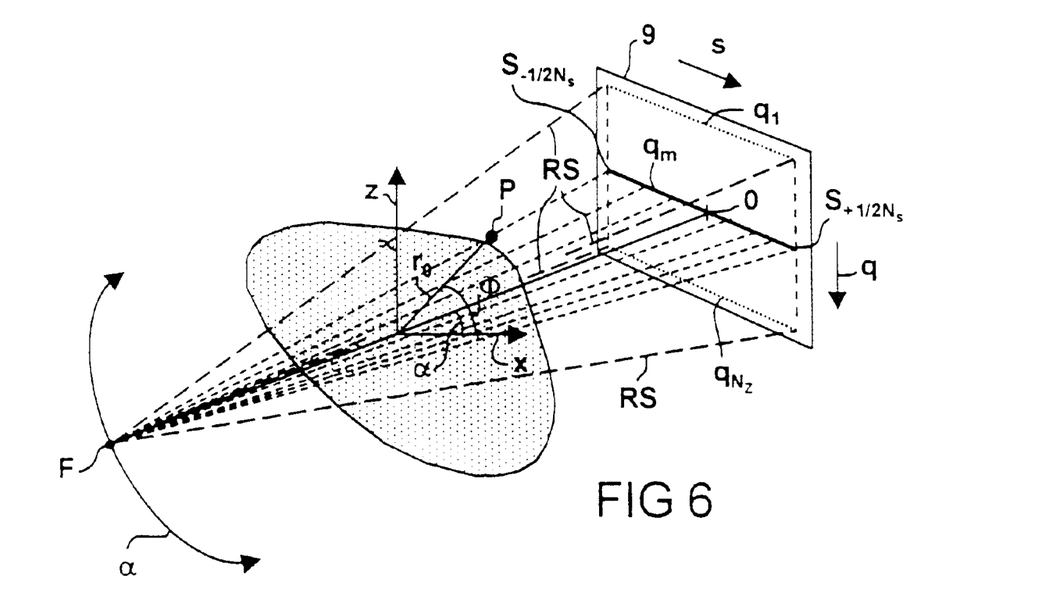
FIGS. 6 and 7 illustrate the geometric relationships employed for the image reconstruction in the inventive x-ray diagnostic device.

In the above described x-ray diagnostic device, the image reconstruction on the basis of measurement data acquired in the disclosed fashion using a detector 9 (according to FIG. 6) exhibiting the detector lines $q_z$ with $q_z=1$ to $N_z$ and per line $N_s$ detector elements (also referred to as channels) proceeds as follows:

The equidistant scanning coordinate of a level x-ray fan (according to FIG. 6) pertaining to a detector line q, of the detector 9 identifies the projection angle s, that extends from $-\frac{1}{2}N_s$ to $+\frac{1}{2}N_s$ with reference to the reconstruction geometry α shown in FIG. 6. It must be taken into account, however, that the scanning coordinate across the angle of beam spread of an x-ray fan pertaining to the one detector line $q_z$ of the detector 9 is not equidistant in the specific case considered, as a result of the implementation of the detector 9 used as a flat image detector.

The x-ray fan (of the conical x-ray beam) pertaining to the center detector line $q_m$ (of the detector 9) lying in the center plane is not slanted toward the detector plane since it lies in the center plane $Z_{img}=0$. The attenuation value $f(r,\phi,z_{img})$ (to be reconstructed) of an image point $r_0=(r,\phi,z_{img})$ lying in the center plane can be found by means of the two dimensional radon-inversion (see A. C. Kak, M. Slaney, "Principles of Computerized Tomographic Imaging", IEEE Press, New York, 1988, pp. 87–91. The designations r, φ and $z_{img}$ identify the coordinates of an image element. The back projection equation is then:

$$f(r, \Phi, z_{img}) = \int_0^{2\pi} \frac{1}{U^2} \cdot Q\alpha(s')d\alpha \qquad (1)$$

with $$Q\alpha(s') = R'_\alpha(s') \otimes g$$

and $$R'_\alpha(s', q_m) = R'_\alpha(s', q_m) \cdot \frac{R_f}{\sqrt{R_f^2 + s'^2}}$$

Thereby, g=½h, whereby h identifies the Shepp and Logan convolution kernel that is common in CT.

Rα(s',$q_m$) is the logarithmic projection value, specified for the virtual detector coordinate s', in the center plane (detector line $q_m$). The virtual detector coordinate s' is the projection emitting from the focus through the image point (r,φ,$z_{img}$) in the detector line $q_m$ on a virtual detector, the detector plane of which contains the system axis Z and runs parallel to the detector plane of the detector 9. In general, s' must be determined by interpolation from measurement signals of neighboring detector elements of the detector 9. Applicable for U is:

$$U = \frac{R_f + r \cdot \sin(\alpha - \Phi)}{R_f}$$

In order to be able to apply the two dimensional radon-inversion equation (equation (1)), the expansion of the detector 9 transverse to the direction of the system axis Z as already mentioned must be so large that the patient P is completely detected by the x-ray beam. For x-ray diagnostic devices of the described herein having an x-ray source 8 and detector 9 attached at an open C-arm 7, this requirement is not fulfilled as a rule so that only one limited area (region of interest ROI) of the patient P can be imaged. This has consequences in turn regarding the convolution kernel h. Since this is not local, but rather has infinite expansion in principle, it cannot be applied here due to the problem of the "truncated projections" (see R. M. Lewitt, R. H. T. Bates, "Image Reconstructions from Projections I: General Theoretical Considerations", Optik, 50, (1978). On the contrary, a convolution kerrel of short reach can be applied, for example, a convolution kernel based on recursive filtering (U. Barth, K. Wiesent in German OS 198 02 850).

If the image point $r_0=(r,\phi,z_{img})$ to be reconstructed does not lie in the center plane, then a weighting factor must be introduced into the equation (1) similar to that for the Feldkamp method, the weighting factor taking into consideration the oblique curve (in the scanned volumes, i.e. sloped toward the center plane) of the x-ray production 9 this image point and pertaining to an x-ray fan slanted toward the center plane.

$$v = \frac{R_s}{\sqrt{R_{s'}^2 + q'^2}} = \frac{R_2}{\sqrt{R_f^2 + s'^2 + q_2'}}$$

wherein q' identifies the z-coordinate (projected on the virtual detector) that is allocated to the x-ray passing through $\underline{r}_0$. $R_{s'}$ is the length of the vertical projection of this x-ray on the center plane. Applicable is:

$$Rs' = \sqrt{R_f^2 + s'^2}$$

The reconstruction equation then reads:

$$f(r, \phi, z_{img}) = \int_0^{2\pi} \frac{1}{U^2} \cdot Q_\alpha(s', z_{img}) d\alpha \quad (2)$$

with $$Q_\alpha(s', z_{img}) = R'_\alpha(s', q') \otimes g$$

(wherein ⊗ denotes the convolution operation)

and $$R'_\alpha(s', q') = R_\alpha(s', q') \cdot \frac{R_f}{\sqrt{R_f^2 + s'^2}} \cdot \frac{R_2}{\sqrt{R_f^2 + s'^2 + q'^2}}$$

the coordinates (s',q') are given on the virtual detector by the projected coordinates of the image point $\underline{r}0=(r,\phi,z_{img})$:

$$s' = R_f \cdot \frac{r \cdot \cos(\alpha - \Phi)}{R_f + r \cdot \sin(\alpha - \Phi)}$$

$$q' = \frac{R_f \cdot (z - z_f(\lambda))}{\sqrt{r^2 + R_f^2 + 2R_f \cdot r \cdot \sin(\alpha - \Phi)}}$$

For the coordinates projected on the virtual detector regarding the actual detector, there is:

$$m_s = s'/\Delta s_s + (N_s - 1)/2$$

and $$m_q = q'/\Delta s_d + (N_z - 1)/2 + \Delta s_d/2$$

Again, $N_z$ is the number of the detector lines and $N_s$ is in turn the number of the channels in a detector line. $\Delta s_s$ is the scanning unit measured on the virtual detector transverse to the direction of the system axis Z, i.e. the distance (measured in the direction of the scanning coordinate) between two neighboring detector elements of a detector line of the virtual detector.

The momentary position $z_f$ of the focus of the x-ray source depends on the period $\lambda$ of the rotation and is given in the projection angle $\alpha$ by:

$$z_f(\alpha, \lambda) = z_{f_0} + pitch \cdot \left( \frac{\alpha}{\pi + \gamma_{fan}} + \lambda \right) \quad (3)$$

The position of the focus at the beginning of the scanning is $z_{f,0}$ and pitch identifies the advance (measured in mm) in the z-direction per period $\lambda$ of the rotation.

The measurement values obtained for a projection angle a and allocated to the coordinates (s',q'($\lambda$)) projected on the virtual detector can be utilized by the computer 15 in a different way for image reconstruction.

For each image point for the image reconstruction, the measurement value that pertains to those coordinates projected on the virtual detector can be selected from that period $\lambda$ of the swivelling, for which the z-distance $|qm-q'(\lambda)|$ and thus the slope of the pertinent x-ray to the center plane assumes the smallest value.

Figure 7:
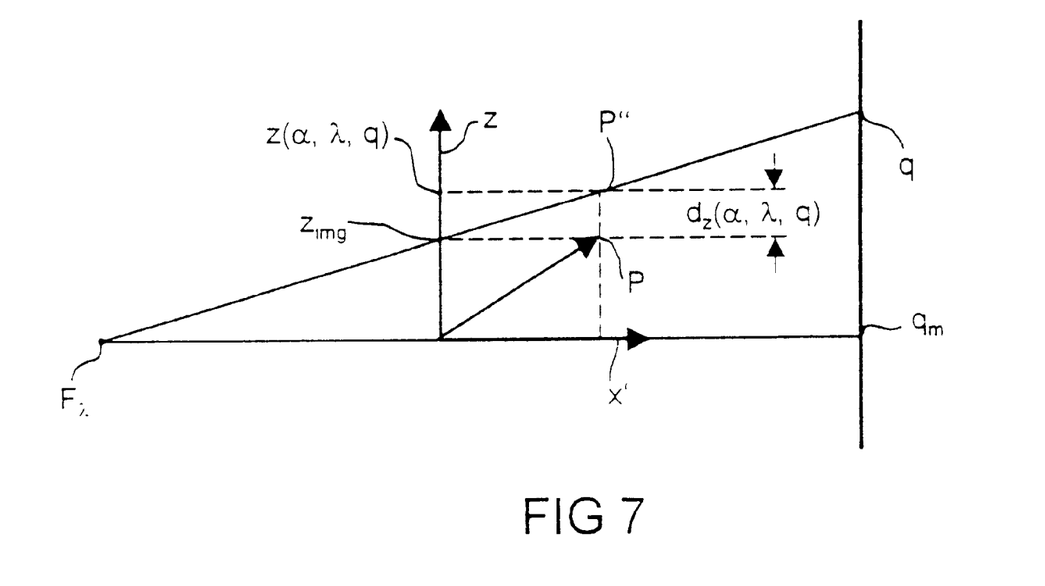

Moreover, several measurement values acquired for the same projection angle by means of different x-rays can be alternatively used for image reconstruction in the course of a weighted average for the respective image point to the extent that the advance in the z-direction is adequately limited (see S. Schaller, "Practical Image Reconstruction for Cone Beam Computed Tomography", Dissertation, Erlangen, 1998), which allows a better utilization of the x-ray dose administered to the patient P. The following is applicable:

The x-ray allocated to the detector line $q_z$ the coordinate s' of which is identical to the vertical projection of the image point P to be reconstructed on the center plane, cuts the straight line (that passes in P parallel to the system axis Z) in point P'''. The difference of the z-value from P''' to the z-value of the image element P defines the z-distance $d_z(\alpha,\lambda,q)$ for the rotation period $\lambda$. In accordance with FIG. 7, this is given by:

$$d_z(\alpha,\lambda,q) = z(\alpha,\lambda,q) - z_{img}$$

For the weighted average of the measurement values acquired by means of several x-rays, a weighting function h is used that can have, for example, a triangular structure:

$$1 - |d_z|/(w\Delta s_d) h(d_z) = 0 \text{ otherwise}$$

The interpolation width w thereby controls the width of the weighting function h in the z-direction.

The corresponding, standardized weighting function h':

$$h' = \frac{h(d_z(\alpha, \lambda, q, z_{img}))}{\sum_{\tilde{\lambda},\tilde{q}} h(d_z(\alpha, \tilde{\lambda}, \tilde{q}, z_{img}))}$$

According the method of the weighted average, the reconstruction is then implemented with generalized projections. These are calculated as:

$$R_\alpha(s', z_{img}) = \sum_{\tilde{\lambda},\tilde{q}} h'(d_z(\alpha, \tilde{\lambda}, \tilde{q}, z_{img})) \cdot R_\alpha(\tilde{s}, \tilde{q}) \cdot \frac{R_{s'}}{\sqrt{R_f^2 + s'^2 + \tilde{q}^2}}$$

Dependent on the interpolation width w, the measurement values from the different periods $\lambda$ of the rotation therefore contribute to the projection value $R_\alpha(s'z_{img})$ The image noise and the resolution in the z-direction can be influenced by the choice of the interpolation width w, whereby the noise decreases with increasing interpolation width w and the resolution in the z-direction increases with decreasing interpolation width w.

In the disclosed exemplary embodiment, a number of adjustment possibilities of the C-arm 7 is provided. Important for the invention, however, is that the C-arm 7 can be rotated around the system axis and the C-arm and the positioning plate 12 can be set up relative to one another such that the shifting of the positioning plate 12 ensues parallel to the direction of the system axis Z.

Moreover, the relative movement between C-arm 7 and positioning plate 12 does not necessarily require the positioning plate 12 is adjusted. On the contrary, there is also the possibility in the scope of the invention to shift the C-arm relative to the positioning plate 12 or to shift both the C-arm 7 as well as the positioning plate 12.

The x-ray source 8 and the detector 9 do not necessarily need to be attached at a C-arm 7. It is only important for the invention is only that the x-ray source 8 and the detector can be swivelled oscillating in tandem around the system axis, whereby such solutions are preferred that permit good access of the medical personnel to a patient P lying on the positioning plate 12. Instead of the positioning plate 12 provided in the case of the disclosed exemplary embodiment, the positioning device can have means of a different type to accept the examination subject.

Instead of the flat image detector provided in the case of the disclosed exemplary embodiment, a different planar detector can be provided, e.g. an x-ray image intensifier.

The disclosed exemplary embodiment is a stationary x-ray diagnostic device. The invention can, however, also be employed in x-ray diagnostic devices wherein at least the C-arm 7 is attached at a base part implemented as a mobile device carriage. Such an x-ray diagnostic device exhibiting a device carriage can be used with a stationary as well as with a mobile patient positioning device, in so far as it is just assured that the disclosed scanning movement can be implemented correctly.

Although modifications and changes may be suggested by those skilled in the art, it is the intention of the inventor to embody within the patent warranted hereon all changes and modifications as reasonably and properly come within the scope of his contribution to the art.

I claim as my invention:

1. An x-ray diagnostic device comprising:

an x-ray source which emits a conical x-ray beam;

a positioning device adapted to receive an examination subject disposed in said x-ray beam;

a two-dimensional radiation detector disposed opposite to said x-ray source for detecting x-rays emitted by said x-ray source and attenuated by said patient, said radiation detector emitting electrical signals dependent on said attenuation;

a mechanism for rotationally oscillating said x-ray source and said radiation detector around a system axis;

a linear displacement mechanism for effecting an uninterrupted linear displacement between said x-ray source and said radiation detector, and said positioning device, substantially along said system axis while said x-ray source and said radiation detector are rotationally oscillating around said system axis; and an image computer supplied with said electrical signals from said radiation detector or reconstructing an image of said examination subject from said signals.

2. An x-ray diagnostic device as claimed in claim 1 comprising an arc-shaped support on which said x-ray source and said radiation detector are mounted, which forms a part of said mechanism for rotationally oscillating said x-ray source and said radiation detector.

3. An x-ray diagnostic device as claimed in claim 1 wherein arc-shaped support comprises a C-arm having a center axis substantially coinciding with said system axis and which is rotated back and forth in a circumferential direction around said center axis for rotationally oscillating said x-ray source and said radiation detector around said center axis.

4. An x-ray diagnostic device as claimed in claim 1 wherein said x-ray source has a focus from which said x-ray beam emanates, and wherein said x-ray beam has an angular beam spread proceeding from said focus in a plane disposed at a right angle to said system axis and containing said focus, and wherein said mechanism for rotationally oscillating said x-ray source and said radiation detector rotationally oscillates said x-ray source and said radiation detector through an angle of at least 180° plus said angular beam spread.

5. An x-ray diagnostic device as claimed in claim 1 wherein said x-ray source and said radiation detector are rotationally oscillated with a period of oscillating movement, and wherein said x-ray source and said radiation detector, and said positioning device, are relatively displaced by a distant $\Delta z_{max}$ per period, wherein $$\Delta z_{max} \leq \Delta_{det} \cdot \frac{R_f - \Delta_{Obj/2}}{R_f + R_d}$$

and $\Delta_{det}$ is a width of the radiation detector in the direction of the system axis, $\Delta_{obj}$ is a span of an area of the examination subject to be scanned measured transverse to the direction of the system axis, $R_f$ is a distance of the focus of the x-ray source from the system axis, and $R_d$ is distance of the radiation detector from the system axis.

6. An x-ray diagnostic device as claimed in claim 1 wherein said x-ray source has a focus from which said x-ray beam emanates, and wherein said image computer calculates individual image points of said image from x-rays passing through said image points in planes at different projection angles, said planes exhibiting a smallest angle relative to a center plane containing said focus and said system axis.

7. An x-ray diagnostic device as claimed in claim 1 wherein said image computer calculates individual image points of said image from x-rays passing through the respective image points in planes at different projection angles, said planes respectively exhibiting different angles relative to said radiation detector and said image points being combined in said image computer by weighted averaging.

* * * * *